(12) United States Patent
John et al.

(10) Patent No.: US 7,939,093 B2
(45) Date of Patent: May 10, 2011

(54) METHOD AND APPARATUS FOR REPRESENTING MYOCARDIAL TISSUES IN DIFFERENT STATES OF DAMAGE

(75) Inventors: Matthias John, Nürnberg (DE); Stefan Lautenschläger, Hausen (DE); Norbert Rahn, Forchheim (DE)

(73) Assignee: Siemens Aktiengesellschaft, Munich (DE)

( * ) Notice: Subject to any disclaimer, the term of this patent is extended or adjusted under 35 U.S.C. 154(b) by 946 days.

(21) Appl. No.: 11/890,400

(22) Filed: Aug. 6, 2007

(65) Prior Publication Data

US 2008/0038197 A1 Feb. 14, 2008

(30) Foreign Application Priority Data

Aug. 9, 2006 (DE) .......................... 10 2006 037 284

(51) Int. Cl.
*A61B 5/05* (2006.01)
(52) U.S. Cl. ......................................... 424/425; 424/9.1
(58) Field of Classification Search .................. 600/425, 600/431–433; 424/9.1, 9.4–9.455
See application file for complete search history.

(56) References Cited

U.S. PATENT DOCUMENTS

| | | | |
|---|---|---|---|
| 5,583,902 A | 12/1996 | Bae | |
| 2003/0028101 A1* | 2/2003 | Weisskoff et al. | ............ 600/431 |
| 2006/0241402 A1* | 10/2006 | Ichihara et al. | ............... 600/425 |

FOREIGN PATENT DOCUMENTS

WO WO 2004/026140 A2 4/2004

OTHER PUBLICATIONS

Andreas H. Mahnken, Ralf Koos, Marcus Katoh, Joachim E. Wildberger, Elmar Spuentrup, Arno Buecker, Rolf W. Günther, Harald P. Kühl, "Assessment of myocardial viability in reperfused acute myocardial infarction using 16-slice computed tomography in comparison to magnetic resonance imaging", Journal of the American College of Cardiology, 2005, pp. 2042-2047, vol. 45, No. 12.
Jean-Francois Paul, Myriam Wartski, Christophe Caussin, Anne Sigal-Cinqualbre, Bernard Lancelin, Claude Angel, Grégoire Dambrin, "Late Defect on Delayed Contrast-enhanced Multi-Detector Row CT Scans in the Prediction of SPECT Infarct Size after Reperfused Acute Myocardial Infarction: Initial Experience", Radiology, 236, 2005, pp. 485-489.

(Continued)

*Primary Examiner* — Brian Casler
*Assistant Examiner* — Parikha S Mehta

(57) ABSTRACT

The invention relates to a method for differentially representing myocardial tissue in different states of damage, comprising the following steps: administering a myocardium-suitable contrast agent to a patient under examination; entering at least one patient-specific parameter affecting the speed of uptake by and elimination from the myocardium of said contrast agent; calculating a point in time after administration of the contrast agent at which a difference between a contrast agent content in necrotic myocardial tissue and a contrast agent content in non-necrotic myocardial tissue attains a maximum value, on the basis of the at least one patient-specific parameter, and carrying out, at the point in time calculated, a late-phase CT scan for accentuation of necrotic myocardial tissue compared to non-necrotic myocardial tissue. The invention likewise relates to apparatus, in particular for carrying out the method.

13 Claims, 2 Drawing Sheets

OTHER PUBLICATIONS

Albert C. Lardo, Marco A.S. Cordeiro, Caterina Silva, Luciano C. Amado, Richard T. George, Anastasios P. Saliaris, Karl H. Schuleri, "Contrast-Enhanced Multidetector Computed Tomography Viability Imaging After Myocardial Infarction: Characterization of Myocyte Death, Microvascular Obstruction, and Chronic Scar", Circulation 2006; pp. 394-404, vol. 113.

Bernhard L. Gerber, MD; Bénédicte Belge, MD ; Gabin J. Legros, Pascal Lim, Alain Poncelet, Agnés Pasquet, Giovanna Gisellu, Emmanuel Coche, Veronica R. Fernandes, Menekhem Zviman, Saman Nazarian, Henry R. Halperin, Katherine C. Wu, Joshua M. Hare, Joao A.C. Lima, "Characterization of Acute and Chronic Myocardial Infarcts by Multidetector Computed Tomography Comparison With Contrast-Enhanced Magnetic Resonance", Circulation 2006 113:823-833.

* cited by examiner

METHOD AND APPARATUS FOR REPRESENTING MYOCARDIAL TISSUES IN DIFFERENT STATES OF DAMAGE

CROSS REFERENCE TO RELATED APPLICATIONS

This application claims priority of German application No. 10 2006 037 284.0 filed Aug. 9, 2006, which is incorporated by reference herein in its entirety.

FIELD OF THE INVENTION

The invention relates to a method and apparatus for representing myocardial tissues in different states of damage.

BACKGROUND OF THE INVENTION

In the industrialized countries, coronary heart disease (CHD) is the most frequent cause of heart failure. Coronary heart disease results in an inadequate supply of blood to the cardiac muscle and possibly to its necrotization because of narrowing of the coronary arteries. Despite much success with drug therapy, direct treatment of the triggering cause constitutes an important therapeutic concept. For CHD patients, the restoration of adequate perfusion by means of revascularization measures such as thrombolysis, stenting, balloon dilation, a bypass operation, etc. is therefore paramount. However, the success of these revascularization measures is dependent on the presence of a vital myocardium downstream of the arterial location treated. While revascularization of vital myocardial areas may improve the pumping function of the heart and the patient's prognosis, revascularization of scar tissue (necrotized) does not produce any improvement in results and constitutes additional risks for the patient.

Precise differentiation between vital and necrotic myocardium is therefore important for the further treatment of patients with an ischemic cardiomyopathy or after a myocardial infarction.

Myocardial tissue areas can be subdivided into the following categories:
(a) normally perfused, i.e. healthy myocardial tissue,
(b) less perfused myocardial tissue which is not or not yet necrotic and
(c) necrotic myocardial tissue (scar tissue).

The differentiation of myocardial tissue into these three groups is relevant to diagnosis and therapy in the field of interventional cardiology and also for electrical electrophysiology, as will be explained below.

Blockages in the coronary arteries which are found e.g. during computed tomography (CT) are nowadays opened using the above-mentioned revascularization measures, which applies to categories b and c. Blockages are therefore opened whose revascularization results in no improvement in the patient's condition, as the myocardial tissue to be supplied is already necrotic and therefore can no longer be reactivated (category c). These operations also pose a risk to the patient, are expensive and have no chance of improving the patient's condition. Only interventions which treat myocardial class b but not myocardial class c are therefore clinically induced. However, this requires reliable, image-based differentiation of the two categories.

Even in the case of electrophysiological ablation procedures for treating ventricular tachycardia (VT ablation) it is advantageous to know the precise position of contours of necrotic myocardial tissue areas, as the pathological conduction centers to be ablated are often in the immediate vicinity of these areas and must be selectively removed there by ablation.

Nowadays magnetic resonance tomography and particularly the nuclear medicine radionuclide techniques of single photon emission computed tomography (SPECT) and positron emission tomography (PET) are standard imaging methods for assessing myocardial vitality. Although new generations of CT scanners are able to record the heart in a breath-hold phase and therefore represent it in an artifact-free manner, they have hitherto had no role in assessing myocardial vitality, even though their basic advantages are known in the prior art.

In general, computed tomography imaging of the heart is the preferred imaging modality for patients with scarred myocardial regions, as pacemakers or implemented defibrillators which frequently occur in the patient profile assumed preclude the use of magnetic resonance imaging, and other modalities such as SPECT or PET provide significantly reduced local resolution. Moreover, using computed tomography is less expensive and its widespread availability even in emergency centers and the possibility of reliable assessment of the extent of the regions in question are further advantages.

It has been shown that if a contrast agent suitable for computed tomography is administered, in the case of a healthy heart the contrast agent is virtually completely eliminated again by the kidneys after a waiting time and a CT scan of the heart carried out after a certain time shows a native image without contrast agent. On the other hand, it has been shown that pathological changes such as stenoses may cause the contrast agent to penetrate much more slowly into the category b and/or c regions affected by the stenosis, but also to be flushed out of these areas more slowly than is the case with healthy tissue.

A possible option for imaging such areas is therefore so-called late enhancement scanning which is performed when a certain time t has elapsed between administration of the contrast agent and the subsequent CT scan, i.e. the CT scan is not performed immediately (in the range of seconds to minutes) after administration of the contrast agent. By detecting such contrast agent increases in late enhancement scan data, an unambiguous assessment is possible as to whether this tissue is myocardium of classification levels a or b (healthy and less perfused) or c (necrotic). Although waiting times of 5 or 15 minutes have been known in the prior art, these waiting times were arbitrarily set.

The problem when using computed tomography for visualizing necrotic myocardial areas lies in the patient-specific optimum waiting time t from administration of contrast agent to image capture in order to differentiate scar tissue in the myocardium.

SUMMARY OF THE INVENTION

The object of the invention is therefore to present an approach with which an optimized CT scan for detecting necrotic myocardial tissue is possible.

This object is achieved according to the invention by the method for differentially representing myocardial tissue in different states of damage and the apparatus for determining the optimum time for carrying out a late-phase CT scan as claimed in the independent claims. Further advantageous embodiments, details and features of the present invention will emerge from the dependent claims, the description and the accompanying drawings.

The invention is based on the principle of determining the optimum time for a late-phase CT scan on the basis of patient-specific parameters.

Accordingly the invention relates to a method for differentially representing myocardial tissue in different states of damage, comprising the following steps:

administering a myocardium-suitable contrast agent to a patient under examination;

entering at least one patient-specific parameter affecting the speed of uptake by and elimination from the myocardium of the contrast agent;

calculating the time after administration of the contrast agent at which a difference between a contrast agent content in necrotic myocardial tissue and a contrast agent content in non-necrotic myocardial tissue attains a maximum value, on the basis of the at least one patient-specific parameter; and carrying out a late-phase CT scan for enhanced detection of necrotic myocardial tissue as compared to non-necrotic myocardial tissue.

By means of the specified method according to the invention it is possible to set the time of the late enhancement CT in such a way that the necrotic myocardial tissue is optimally contrasted.

Patient-specific parameters can be acquired either by an inputting means and manual input of manually determined patient parameters or by automatic acquisition by suitable measuring instruments. For automation and routine use of the method, it is advisable to acquire automatically the patient parameters to be acquired.

The essence of the invention consists in calculating the time at which the difference between the contrast agent content in necrotic myocardial tissue and a contrast agent content in non-necrotic myocardial tissue attains a maximum value, the patient-specific parameters being used for this calculation in addition to basic assumptions. In this way it is possible to determine for each patient and each examination (type and quantity of contrast agent) the point in time after administration of a contrast agent when the contrast is at its most pronounced in necrotic myocardial tissue compared to the contrast in the other tissue categories. This enables the myocardium to be visualized in the most contrasty manner possible.

In a preferred embodiment, the method can include the following additional step: performing immediately after contrast agent administration an early-phase CT scan for enhanced detection of normally perfused myocardial tissue compared to less perfused and necrotic myocardial tissue.

"Immediately after contrast agent administration" is to be understood as meaning that the CT scan is carried out either without delay or at least so soon after contrast agent administration that no metrologically relevant uptake of contrast agent by category C necrotic myocardial tissue has taken place.

This preferred embodiment of the invention makes it possible to distinguish between normally perfused myocardial tissue of category a and myocardial tissue of categories b and c which can be differentiated by so-called first pass data. At the given point in time immediately after contrast agent administration, the tissue of categories b and c is characterized by lower contrast agent enhancement compared to category a tissue. On the other hand, the distinction between a+b and c was able to be made on the basis of late-phase CT scans and the data determined thereby, where category c tissue is characterized by higher contrast agent enhancement compared to tissue of categories a and b. If the information from the two scans is combined, each myocardial area can be clearly identified and classified. In another preferred embodiment, the invention therefore includes the following additional step:

calculating a subtraction data record from the data of the early-phase CT scan and the late-phase CT scan for enhanced representation of less perfused myocardial tissue.

By means of this additional calculation step which identifies less perfused myocardial tissue, it is possible to distinguish all three categories from one another by reapplying this data to the data records of the early- and late-phase CT scan.

As patient-specific parameters, the following variables, at least one of which is entered and used for the calculation, have been determined by the inventors:

pulse,
blood pressure,
respiration,
ventricular volume,
cardiac output,
quantity and type of contrast agent administered,
patient's body size and weight.

In preferred embodiments, a plurality of, e.g. two, three or four, or all these parameters are entered and used to calculate the maximum value of the difference between contrast agent content in necrotic myocardial tissue and non-necrotic myocardial tissue.

The method can preferably include the following farther step: extraction of the contours of areas of necrotic myocardial tissue from the late enhancement scan data.

This step concludes the method according to the invention in that the differentiation of categories a, b and c necessary for treatment is thus complete.

The method can likewise contain the step of visualizing necrotic, less perfused or normally perfused myocardial areas by means of a computer-based display means, it being possible to use different types of representation and display means which are known in principle to persons skilled in the art.

The maximum value of the difference in contrast agent content is preferably calculated using the following formula: the parameters m, n and o can be determined by empirical studies (e.g. mass examination), by including at least one patient-specific parameter (blood pressure, etc.).

$$S_{m,n,o}(t) = m \cdot e^{\frac{(t+t_{const})}{-n}} \cdot (t + t_{const})^o$$

where S(t) is a time-dependent approximation function for contrast agent signal intensity versus time, m, n and o are constants derived from the patient-specific parameters, t the time with which the contrast agent signal intensity varies, calculated with zero at $t_{const}$; and $t_{const}$ is a time after which the contrast agent has been flushed out of normally and less perfused myocardial tissue, t being varied until S(t) is in a typical grayscale range for imaging necrotic myocardial tissue.

The parameters m, n, o are derived from patient specific parameters x1, x2, x3, ..., written as m(x1, x2, x3, ...), n(x1, x2, x3, ...), o(x1, x2, x3, ...). The functions can be assumed as approximating model functions, e.g. polynomial functions or piecewise polynomial function like Splines. To model these function, additional parameters are needed, e.g. y_m, y_n, y_o and therefore have m(x1, x2, x3, ..., )=m(x1, x2, x3, ..., y_m), n(x1, x2, x3, ...)=n(x1, x2, x3, ..., y_n), o(x1, x2, x3, ...)=o(x1, x2, x3, ..., y_o). Given an empirical study, where the signal intensity S(t) is determined for several patients and time points t and therefore for several sets of parameters x1, x2, x3, ..., the functions m(x1, x2, x3, ...), n(x1, x2, x3, ...), o(x1, x2, x3, ...) can be approximated by computing the following equations:

$$S(1)=S(t1, x1, y\_m, y\_n, y\_o) \text{ with measured values } S(1), t1, x1 \text{ and unkown parameters } y\_m, y\_n, y\_o.$$

$$S(2)=S(t2, x2, y\_m, y\_n, y\_o) \text{ with measured values } S(2), t2, x2 \text{ and unkown parameters } y\_m, y\_n, y\_o.$$

$$S(3)=S(t3, x3, y\_m, y\_n, y\_o) \text{ with measured values } S(3), t3, x3 \text{ and unkown parameters } y\_m, y\_n, y\_o.$$

Numerical solvers like the Levenberg-Marquardt-Algorithm can be used for solving this non-linear equation.

It is particularly preferred here that S(t) lies approximately in the middle of the grayscale range of the scan.

The invention further relates to an apparatus, all the statements relating to the method also applying to said apparatus and vice versa, so that reference will be made alternately.

The inventive apparatus for determining the optimum point in time for carrying out a late-phase CT scan for highlighting necrotic myocardial tissue compared to non-necrotic myocardial tissue in a patient comprises:
- at least one inputting means for entering at least one patient-specific parameter affecting the speed of uptake by and elimination from the myocardium of a contrast agent administered to the patient; and
- a computing unit for calculating the optimum point in time after administration of the contrast agent as the point in time at which a difference between a contrast agent content in necrotic myocardial tissue and a contrast agent content in non-necrotic myocardial tissue attains a maximum value; on the basis of the at least one patient-specific parameter.

The inputting means can be optionally a manual inputting means with which an operator of the apparatus enters the patient-specific parameters into the apparatus, or can be at least one sensor for acquiring at least one patient-specific parameter affecting the speed of uptake by and elimination from the myocardium of a contrast agent administered to the patient. It is also possible for the inputting means to be a combination of the two above described possibilities, i.e. certain parameters are automatically acquired by sensors, while others are entered manually. It is conceivable, for example, to provide the apparatus with sensors for measuring pulse and respiration as well as blood pressure, while the quantity and type of contrast agent administered are entered manually via a keyboard or some other input device.

The computing unit is designed and configured in particular to carry out the above-described method of calculating the optimum point in time, but can also additionally undertake other functions such as directly controlling the CT scanner. The computing unit can also be implemented as part of the normal control system of a CT scanner, e.g. as a software module.

In addition, the apparatus according to the invention preferably contains a stop function for counting down the period of time between contrast agent administration and the calculated optimum time.

The stop function is used to provide a signal if the period of time to optimum measurement by the late-phase CT scan has elapsed. When this time has elapsed, the stop function can produce a signal so that a user of the CT scanner activates said scanner. However, the apparatus according to the invention can also incorporate a control unit for initiating the late-phase CT scan, said control unit automatically activating the scanner after activation of the stop function and the elapsing of the time period.

In a specific embodiment, the method according to the invention is carried out as follows:
1. Before the start of CT scanning: elicitation of patient-specific parameters affecting the time characteristic of the enhancement and depletion of the contrast agent in the necrotic areas.
2. Determining the time t which is to elapse between contrast agent administration and a late-phase CT scan, as a function of the above-mentioned parameters or a subset of these parameters using a calculation or optimization algorithm which is executable on a workstation connected to the CT scanner or on the CT scanner itself and determines the time t according to the invention.
3. Automatic starting of the CT scan after the elapse of time t after contrast agent administration or manual starting of the CT scan by the examining clinician after the elapse of time t, this time being displayed on the examination monitor or counted down.
4. When the reconstructed CT data record is available, extraction of the contours of the necrotic myocardial areas.
5. Visualization of the necrotic myocardial areas, e.g. in a 3D visualization of the myocardial tissue or in a 3D visualization of the endocardial tissue or in a polar map visualization of the myocardial tissue.

According to the invention it is essential here, in order to be able differentiate precisely between myocardial classes a and b and c in late enhancement scan data, to know the ideal waiting time t between contrast agent administration and the scan, as this is the only way to achieve a maximum grayscale difference $\Delta HU = HU_{(c)} - HU_{(a+b)}$ which facilitates differentiation.

The contrast agent enhancement in myocardial tissue for all the myocardial classes can be described by the following formula:

$$KM_{\alpha,\beta,\chi,\delta}(t) = \alpha \sin(\beta t)\exp(\chi t + \delta)$$

where
- KM(t) is the time- and parameter-dependent function describing the quantity of contrast agent in the myocardial tissue,
- $\alpha, \beta, \chi, \delta$ are patient-specific parameters which have different values for different myocardial classes; and
- t is the time with which the signal intensity of the imaged contrast agent varies.

Note that the parameters $\alpha, \beta, \chi, \delta$ have different values for different myocardial classes. In order to determine the ideal time t at which $\Delta HU$ is maximum, t at which $$\Delta KM(t) = KM_{\alpha_c,\beta_c,\chi_c,\delta_c}(t) - KM_{\alpha_{a+b},\beta_{a+b},\chi_{a+b},\delta_{a+b}}(t)$$

is maximum must be determined.

BRIEF DESCRIPTION OF THE DRAWINGS

Preferred embodiments of the invention are described below by reference to the accompanying drawings: The drawings show.

DETAILED DESCRIPTION OF THE INVENTION

Figure 1:
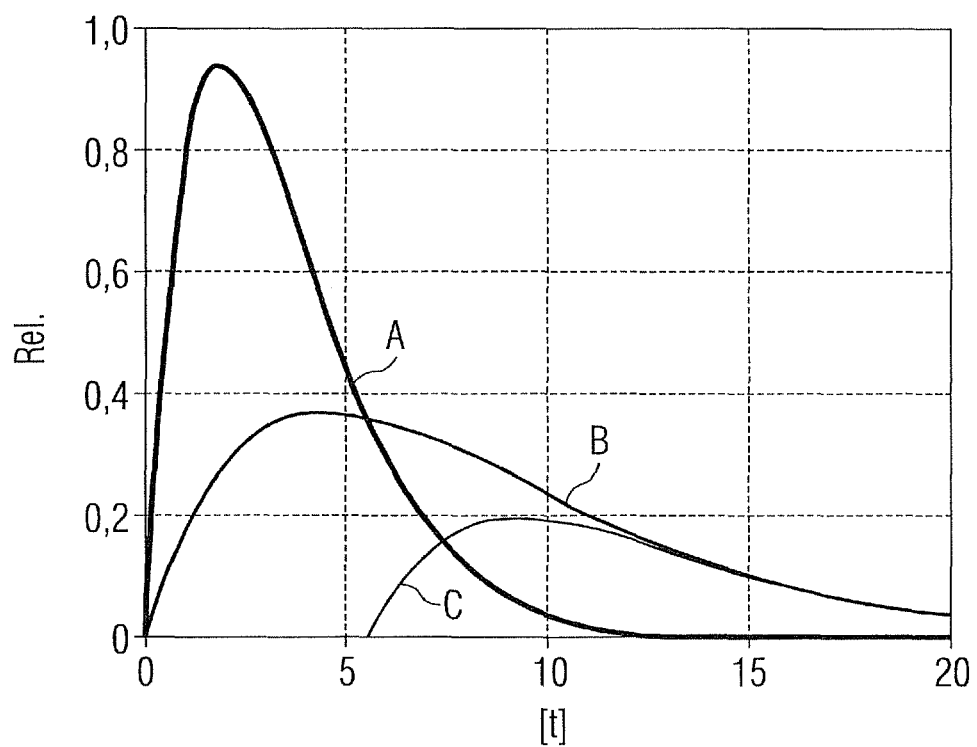
FIG. 1 a typical contrast agent characteristic for vital and necrotic myocardium and the difference between the two contrast concentrations, and FIG. 2 an apparatus for determining a time for performing a late-phase CT scan of a myocardial tissue of a patient.
Figure 2:
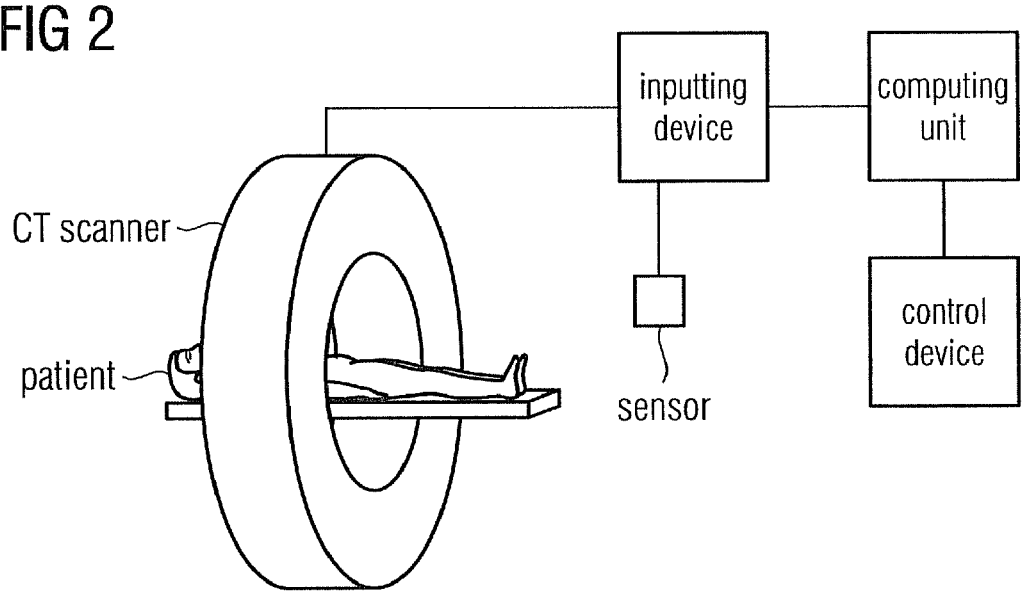

FIGURE shows a typical contrast agent characteristic for vital and necrotic myocardium and the difference between the two contrast concentrations. The curve A shows the contrast agent characteristic for normally perfused myocardium and less perfused myocardium, while the curve B shows the time-delayed and weaker response of the contrast agent for necrotic myocardium and finally the curve C shows the difference between the two curves A and B, the peak of the curve C representing the maximum value of the difference in contrast agent content to be determined according to the invention, and indicates the point in time of this maximum value at which a late-phase CT scan must be carried out for optimum image results.

The invention permits the visualization of necrotic myocardial areas using CT scans which are initiated after a particular patient-specific waiting time, determined by the invention, after the administration of contrast agent.

The present invention thus enables myocardial classes a, b and c to be differentiated using CT, thereby making visualization of necrotic myocardial areas possible so that blockages in coronary arteries can be selectively treated on the basis of the classification of the myocardial areas supplied by the coronaries affected or ablations can be selectively carried out in the edge region of necrotic myocardial areas during electrophysiological VT procedures.

The invention claimed is:

1. A method for representing a myocardial tissue of a patient, comprising:
   administering a contrast agent to the patient;
   inputting a patient-specific parameter that relates to a speed of perfusing the contrast agent by a myocardial tissue and eliminating the contrast agent from the myocardial tissue;
   calculating a time at which a difference between a content of the contrast agent in a necrotic myocardial tissue and in a non-necrotic myocardial tissue attains a maximum value based on the patient-specific parameter;
   performing a late-phase CT scan for detecting the necrotic myocardial tissue compared to the normally perfused myocardial tissue at the calculated time; and
   representing the necrotic myocardial tissue and the normally perfused myocardial tissue for medically examining the patient,
   wherein the maximum value of the difference in the content of the contrast agent is calculated by:

$$S_{m,n,o}(t) = m \cdot e^{\frac{(t+t_{const})}{-n}} \cdot (t + t_{const})^o$$

wherein:
   S(t) is a time-dependent approximation function for a response of a contrast agent signal intensity versus time,
   m, n and o are constants derived from the patient-specific parameters,
   $t_{const}$ is a time after which the contrast agent has been flushed out of the normally and the less perfused myocardial tissues, and
   t is the time with which the contrast agent signal intensity varies and is zero at $t_{const}$.

2. The method as claimed in claim 1, further comprising performing an early-phase CT scan for detecting the normally perfused myocardial tissue compared to a less perfused myocardial tissue and the necrotic myocardial tissue immediately after administering the contrast agent.

3. The method as claimed in claim 2, wherein a subtraction data record is calculated from the early-phase CT scan and the late-phase CT scan for detecting the less perfused myocardial tissue.

4. The method as claimed in claim 2, wherein the early-phase CT scan and the late-phase CT scan are displayed on a display device.

5. The method as claimed in claim 1, wherein the patient-specific parameter is selected from the group consisting of: pulse, blood pressure, respiration, ventricular volume, cardiac output, amount and type of the contrast agent, body size, and weight.

6. The method as claimed in claim 1, wherein a contour of areas of the necrotic myocardial tissue is extracted from the late-phase CT scan data.

7. The method as claimed in claim 1, wherein t is varied until S(t) is in a typical grayscale range in an image of the necrotic myocardial tissue.

8. The method as claimed in claim 1, wherein S(t) is approximately in a middle of a grayscale range of an image of the myocardial tissue.

9. An apparatus for determining a time for performing a late-phase CT scan of a myocardial tissue of a patient, comprising:
   an inputting device that inputs a patient-specific parameter related to a speed of perfusing a contrast agent by a myocardial tissue and eliminating the contrast agent from the myocardial tissue;
   a computing unit that calculates a time at which a difference between a content of the contrast agent in a necrotic myocardial tissue of the patient and a normally perfused myocardial tissue of the patient attains a maximum value based on the patient-specific parameter;
   a CT scanner that performs a late-phase CT scan for detecting the necrotic myocardial tissue compared to the normally perfused myocardial tissue and an early-phase CT scan for detecting the normally perfused myocardial tissue compared to a less perfused myocardial tissue immediately after administering the contrast agent; and
   a control device that activates the CT scanner for performing the late-phase CT scan when a time period between administering the contrast agent and the calculated time has elapsed,
   wherein the maximum value of the difference in the content of the contrast agent is calculated by:

$$S_{m,n,o}(t) = m \cdot e^{\frac{(t+t_{const})}{-n}} \cdot (t + t_{const})^o$$

wherein:
   S(t) is a time-dependent approximation function for a response of a contrast agent signal intensity versus time,
   m, n and o are constants derived from the patient-specific parameters,
   $t_{const}$ is a time after which the contrast agent has been flushed out of the normally and the less perfused myocardial tissues, and
   t is the time with which the contrast agent signal intensity varies and is zero at $t_{const}$.

10. The apparatus as claimed in claim 9, wherein the inputting device comprises a sensor that acquires the patient-specific parameter.

11. The apparatus as claimed in claim 9, wherein the patient-specific parameter is selected from the group consisting of: pulse, blood pressure, respiration, ventricular volume, cardiac output, amount and type of the contrast agent, body size, and weight.

12. The apparatus as claimed in claim 9, wherein t is varied until S(t) is in a typical grayscale range in an image of the necrotic myocardial tissue.

13. The apparatus as claimed in claim 9, wherein S(t) is approximately in a middle of a grayscale range of an image of the myocardial tissue.

* * * * *